US012575967B2

(12) United States Patent
Laffitte et al.

(10) Patent No.: US 12,575,967 B2
(45) Date of Patent: Mar. 17, 2026

(54) NEEDLE INSERTION DEVICE FOR THE ELECTROPORATION OF A PRODUCT INTO AN EYE

(71) Applicant: EYEVENSYS, Paris (FR)

(72) Inventors: Jean-Denis Laffitte, Etampes (FR); Francine Behar-Cohen, Paris (FR); Christophe Moureaux, Besancon (FR); François Cabaud, Ecole Valentin (FR); Jerome Joseph Schafer, Liberty Township, OH (US); Travis Michael Craft, Loveland, OH (US); Benjamin Lee Ko, Cincinnati, OH (US); Jacob William Schubert, Bellevue, KY (US); Michael D. Auld, Milford, OH (US)

(73) Assignee: EYEVENSYS, Paris (FR)

( * ) Notice: Subject to any disclaimer, the term of this patent is extended or adjusted under 35 U.S.C. 154(b) by 1037 days.

(21) Appl. No.: 17/604,824

(22) PCT Filed: Apr. 24, 2020

(86) PCT No.: PCT/EP2020/061481
§ 371 (c)(1),
(2) Date: Oct. 19, 2021

(87) PCT Pub. No.: WO2020/216915
PCT Pub. Date: Oct. 29, 2020

(65) Prior Publication Data
US 2022/0202612 A1 Jun. 30, 2022

(30) Foreign Application Priority Data
Apr. 26, 2019 (EP) ..................................... 19171399

(51) Int. Cl.
A61F 9/00 (2006.01)
A61N 1/30 (2006.01)
A61N 1/32 (2006.01)

(52) U.S. Cl.
CPC ............ A61F 9/0017 (2013.01); A61N 1/306 (2013.01); A61N 1/327 (2013.01)

(58) Field of Classification Search
CPC .................. A61F 9/0017; A61F 9/0008; A61F 2009/0052; A61N 1/327; A61N 1/306;
(Continued)

(56) References Cited

U.S. PATENT DOCUMENTS 9,180,044 B2 11/2015 Touchard et al.
2011/0152749 A1 * 6/2011 Touchard .............. A61F 9/0008
604/116
(Continued)

FOREIGN PATENT DOCUMENTS

EP 2767307 A1 * 8/2014 ........... A61F 9/0017
EP 3081198 A1 10/2016
(Continued)

OTHER PUBLICATIONS

International Search Report (ISR) for PCT/EP2020/061481 mailed Sep. 11, 2020 (6 pages).
(Continued)

*Primary Examiner* — Chelsea E Stinson
*Assistant Examiner* — Nelson Louis Alvarado, Jr.
(74) *Attorney, Agent, or Firm* — Jason A. Smith; Shumaker, Loop & Kendrick, LLP

(57) ABSTRACT
A device including a support (4) comprising a support base defining a spherical base contact surface, extending along a virtual sphere (S) and a circular rim extending in a rim plane; a first and a second needle mobile on the support between extracted and inserted positions in which the first and second
(Continued)

needles are outside and maximally inserted in said virtual sphere, respectively, via first and second intermediate piercing positions in which, respectively, the first and second needles extend along first and second insertion axis and their tips are located on first and second insertion points belonging respectively to first and second hemispheres of the virtual sphere separated by a "median radial plane of the rim", an angle ($\theta$) between the median radial plane and any insertion axis being between 70° and 110°.

13 Claims, 11 Drawing Sheets

(58) Field of Classification Search
CPC .............. A61N 1/0526; A61N 1/0424; A61M 2210/0612; A61M 37/0015; A61M 2037/0007; A61M 2037/0023; A61M 2037/0046; A61B 2018/00613
See application file for complete search history.

(56)                References Cited

U.S. PATENT DOCUMENTS

2014/0316326 A1 * 10/2014 Behar-Cohen ........ A61F 9/0026
                                                                604/21
2015/0238356 A1     8/2015 Touchard et al.
2018/0289958 A1 * 10/2018 Lebreton .............. A61F 9/0008

FOREIGN PATENT DOCUMENTS

WO        2006123248 A2    11/2006
WO        2009122030 A1    10/2009
WO        2016166172 A2    10/2016

OTHER PUBLICATIONS

Written Opinion for PCT/EP2020/061481 mailed Sep. 11, 2020 (11 pages).

* cited by examiner 54
57₂
57₁
6a
6b

C
Y
54
62'
57₂
57₁

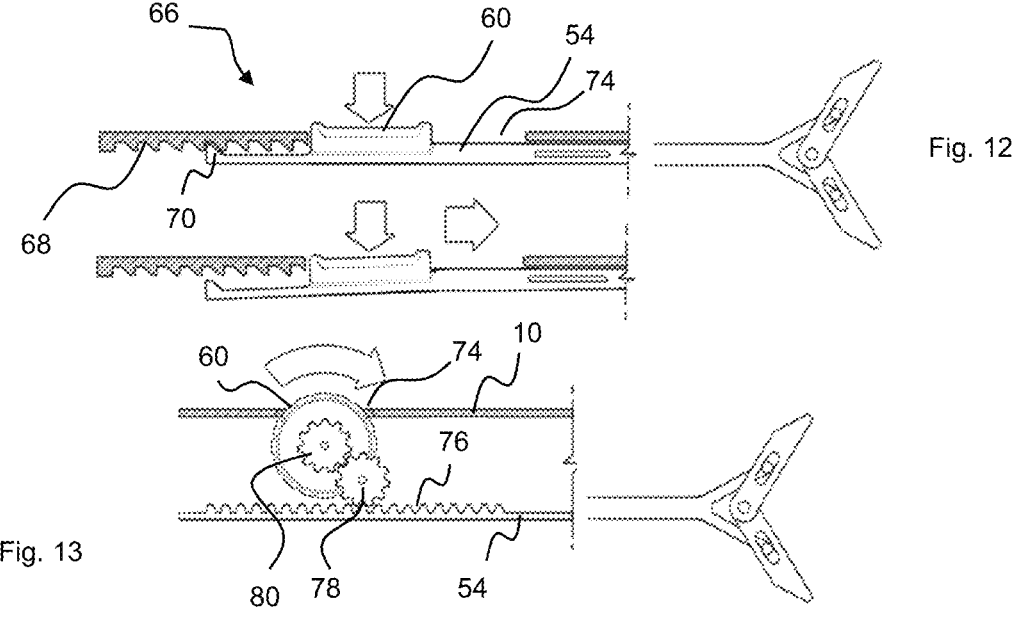
Fig. 12
Fig. 13
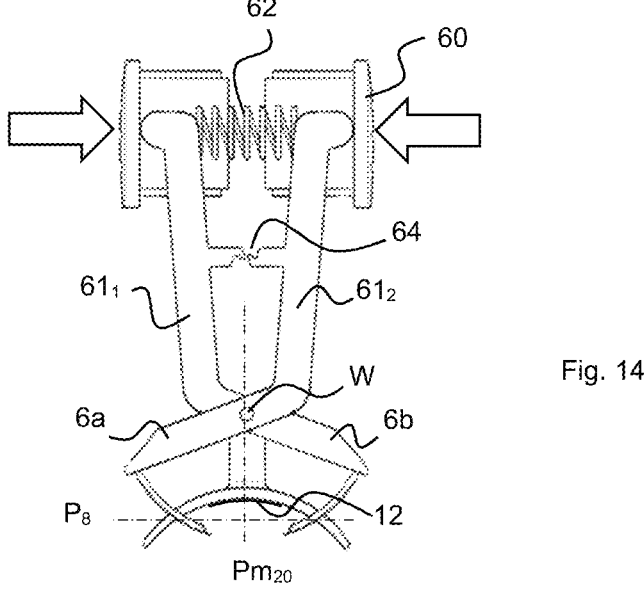
Fig. 14

1

NEEDLE INSERTION DEVICE FOR THE ELECTROPORATION OF A PRODUCT INTO AN EYE

TECHNICAL FIELD

The present invention relates to an insertion device to insert needles in an eye, in particular to insert electrode needles of an electroporation device for injecting a product into a ciliary muscle of the eye.

BACKGROUND

WO 2016/166172 discloses an electroporation device for injecting a product into a ciliary muscle of the eye. This device enables a precise and stable positioning of electrode needles into said eye.

However, each needle is inserted substantially tangentially to the surface of the eye. The impact of the needle when it hits the surface may therefore lead to a rotation of the eye, which hinders the insertion on the needles.

Clamps are known to maintain the eye. However, they are bulky and require an extra operator.

There is a need for a solution which would facilitate the insertion of the needles, without the above-mentioned drawbacks.

It is an object of the invention to answer to this need.

SUMMARY OF THE INVENTION

To this end, the invention proposes a device, preferably an electroporation device, comprising:
- a support comprising a support base defining
  - a spherical base contact surface extending along a virtual sphere having a radius between 10 and 15 mm to match an outside surface of an eye, and
  - a circular rim extending in a rim plane, having an axis X and a radius of greater than 5 mm and of less than 8 mm, so as to match the limbus of the eye;
- a first needle and a second needle having a first tip and a second tip, respectively, and being mobile on the support between
  - first and second extracted positions, in which the first and second needles are outside said virtual sphere, respectively, and
  - first and second inserted positions, in which the first and second needles are maximally inserted in the virtual sphere, respectively,
  - via first and second intermediate piercing positions in which, respectively, the first and second needles extend along first and second insertion axis and the first and second tips are located on first and second insertion points belonging respectively to first and second hemispheres of the virtual sphere which are separated by a plane including the axis X and including a central point at mid-length of the rim, or "median radial plane of the rim".

In a first aspect of the invention, the first and second needles are mobile on the support so that, during an insertion operation starting from the first and second extracted positions and ending at the first and second inserted positions, the first and second needles compress, or "pinch", the virtual sphere toward the median radial plane of the rim when they reach the first and second intermediate piercing positions.

Preferably, an angle θ between the median radial plane of the rim and any of the first and second insertion axis is greater than 10°, preferably greater than 20°, preferably greater than 30°, preferably greater than 40°, preferably greater than 50°, and/or less than 170°, preferably less than 160°, preferably less than 150°, preferably less than 140°, preferably less than 130°, preferably less than 120°, preferably less than 110°.

In a second aspect of the invention, an angle between the median radial plane of the rim and any of the first and second insertion axis is greater than 70° and less than 110°. This embodiment is particularly advantageous when the first and second needles are straight, as represented in FIGS. 1 to 6.

Whatever the aspect of the invention, when the spherical contact surface is extending on the outside surface of the eye, the first and second tips therefore compress the eye as they are being pushed on the outside surface of the eye.

As it will become clear in the following description, the compression action advantageously limits the risk of rotation of the eye during the insertion of the first and second needles. In addition, the compression of the eye may be simultaneous to the insertion of the tips inside the eye, so that both compression and insertion operations can be achieved by a single operator.

A device according to the second aspect of the invention may also have one or several of the following optional and preferred features:
- an angle between
  - the median radial plane of the rim and
  - the insertion axis of the first needle, preferably of any first needle and/or of the second needle, preferably of any second needle
- is greater than 70°, 80°, or 85° and/or less than 110°, 100°, or 95°, preferably about 90°, the first and second needles being preferably aligned;
- an angle between
  - the rim plane, and
  - the first needle, preferably any first needle and/or the second needle, preferably any second needle
- is less than 20°, preferably less than 10°, preferably less than 5°;
- the device comprises a first and/or a second resilient member arranged to act on the first and/or second needles, respectively, to move the first and/or second needles toward the first and/or second extracted positions, respectively;
- the device comprises first and second resilient members configured to substantially apply the same force on the first and second needles, respectively, said force being greater than 1 Newton and less 10 Newton;
- when all the first and second needles are in the inserted position, the first needles are interlaced with the second needles, and/or, preferably inside the virtual sphere, the first needles substantially extend along the whole length of the second needles, and conversely, or
  - alternatively, when all the first and second needles are in the inserted position, the distance between the first tip of a first needle and the second tip of a second needle is less than 1 mm, preferably less than 0.5 mm;
- the device is an electroporation device and comprises an electric generator, an invasive electrode electrically connected to a first terminal of the electric generator and comprising said first and second needles, the support also comprising a plate electrode connected to a second terminal of the electric generator and defining a plate electrode contact surface which extends along the virtual sphere;
- the device comprises a plurality of first needles, preferably extending in a first needle plane, preferably parallelly to each other, and/or a plurality of second needles, preferably extending in a second needle plane, preferably parallelly to each other, all first needles and second needles preferably extending in a common needle plane, preferably parallelly to each other;

the first needle plane and/or the second needle plane and/or the common needle plane defines with the median radial plane of the rim, an angle greater than 70°, 80°, or 85° and/or less than 110°, 100°, or 95°, preferably about 90°, and/or with the rim plane an angle which is greater than 40° and less than 80°;

the device comprises an electroporation generator comprising first and second terminals with different polarities, an invasive electrode electrically connected to the first terminal and comprising said first and second needles, a plate electrode fixed on the support, connected to the second terminal, and defining a plate electrode contact surface which extends along the virtual sphere, the dimensions of the plate electrode contact surface being preferably such that the plate electrode contact surface substantially extends in a general "plate electrode plane".

the first needle plane and/or the second needle plane and/or the common needle plane is substantially parallel to the plate electrode plane;

the plate electrode extends in a plane and the first needle plane and/or the second needle plane and/or the common needle plane is substantially parallel to the plane of the plate electrode;

when all first and second needles are in their inserted position, i.e. in the configuration of full insertion of said needles, the distance between the needles and the plate electrode plane is between 2.0 and 1.3 mm, preferably between 1.8 and 1.5 mm, preferably between 1.7 and 1.6 mm, and is preferably substantially constant whichever point of the plate electrode is being considered;

the distance between the rim and any point of the plate electrode contact surface is greater than 2 mm and less than 6 mm;

the device comprises an injection needle, the support base comprising a guide conformed to guide a sliding of the injection needle between a retrieved position and an injection position in which a tip of the injection needle is outside and inside the virtual sphere, respectively;

preferably, in the injection position, the part of the injection needle which extends inside the virtual sphere extends in a plane, preferably a median plane, between the common needle plane and the plate electrode plane; preferably parallel to the first and second needles;

when the plate electrode is extending in contact with the outside surface of the eye and the rim is extending on the limbus of the eye, and the injection needle is fully inserted (injection position), the ejection orifice of the injection needle opens in the ciliary muscle of the eye;

the first and second needles are fixed to first and second comb bases, respectively, which in the inserted position of the first and second needles, are substantially symmetric relative to median radial plane of the rim;

in the inserted position of the first and second needles (i.e. configuration of full insertion, or "inserted position"), when observing said device along an observation direction perpendicular to the plate electrode plane, each needle appears to cross the entire plate electrode contact surface.

The features of the different aspects of the invention may be combined. In particular, the optional features of a device according to the second aspect of the invention may be applied to a device according to the first aspect of the invention.

A device according to the first aspect or to second aspect of the invention may also have one or several of the following optional and preferred features:

the device comprises first and second comb bases on which the first and second needles are rigidly fixed, respectively;

the device comprises first and second arms supporting the first and second needles (or the first and second comb bases), respectively, the second arm being rotationally mounted on the first arm, around an axis, or the first and second arms being rotationally mounted on the support base around different respective axis, or the first and second arms being mounted so as to translate on the support base, preferably along a common direction;

the device comprises a spring elastically needles toward the first and second extracted positions, respectively, the spring acting, for instance, on the first and second comb bases;

the device comprises a synchronisation mechanism to synchronize the movements of the first and second needles during said insertion operation, in particular to synchronize the movement of the first and second comb bases on which the first and second needles are rigidly fixed, respectively;

the synchronisation mechanism comprises a connector having first and second branches mechanically coupled with the first and second comb bases on which the first and second needles are rigidly fixed, respectively;

the first and second branches define first and second pins slidingly mounted in first and second guide rails defined by the first and second comb bases, respectively, or the first and second comb bases are linked by an elastic junction and the first and second branches are slidingly mounted on the first and second comb bases, respectively, so as to push said first and second comb bases against the action of the elastic junction;

the first and second comb bases and the elastic junction together constitute a leaf spring;

the device comprises a deactivable lock to lock the synchronization mechanism at least in an extracted configuration in which the first and second needles are in the first and second extracted positions and/or in an inserted configuration in which the first and second needles are in the first and second inserted positions;

the device comprises an actuator configured for an operator to act on the synchronisation mechanism, so as to simultaneously move the first and second needles;

the device comprises a drive mechanism defining a plurality of predetermined positions in which the first and second needles can be immobilized during the insertion operation.

In an embodiment, the first needle and/or the second needles are curved, preferably so as to extend along a common circle, which is particularly advantageous when the first and second needles are arranged so as to rotate on the support, preferably around a common rotation axis close to or containing the centre of said circle, during said insertion operation. Preferably, the distance between said common rotation axis and the centre of said circle is less than 5 mm, preferably less than 3 mm, preferably less than 2 mm, preferably less than 1 mm.

Preferably, in the inserted position of a curved first needle, the distance between any point of said first needle facing the plate electrode and the plate electrode is greater than 0.8 mm, preferably greater than 0.9 mm, preferably greater than 1.0 mm, and/or less than 2.0 mm, preferably less than 1.9 mm, preferably less than 1.8 mm, preferably less than 1.7 mm.

Preferably, in the inserted position of any curved first needle, the distance between any point of said first needle facing the plate electrode and the plate electrode is greater than 0.8 mm, preferably greater than 0.9 mm, preferably greater than 1.0 mm, and/or less than 2.0 mm, preferably less than 1.9 mm, preferably less than 1.8 mm, preferably less than 1.7 mm.

Preferably, in the inserted position of any curved second needle, the distance between any point of said second needle facing the plate electrode and the plate electrode is greater than 0.8 mm, preferably greater than 0.9 mm, preferably greater than 1.0 mm, and/or less than 2.0 mm, preferably less than 1.9 mm, preferably less than 1.8 mm, preferably less than 1.7 mm.

Preferably, in the inserted position of first needle(s), the distance between any point of said first needle(s) facing the plate electrode and the plate electrode is substantially constant. In particular, in an embodiment, the first needle(s) is (are) curved and the plate electrode is curved so that the distance between any point of said first needle(s) facing the plate electrode and the plate electrode is substantially constant. In particular, the plate electrode may be convex, i.e. have a curvature centre which is outside the virtual sphere.

Definitions

The "compression forces" corresponds to the forces applied by the needles on the surface of an eye when said needles are moving from the extracted position to the inserted position and push on said surface before piercing it.

The "insertion point" of a needle is the point where, in piercing position, the insertion axis along which said needle extends crosses the virtual sphere bearing the contact surface.

Two needles are "aligned" when they extend on a same axis.

A "quadrant of a hemisphere" designates a quarter of the surface of this hemisphere obtained by cuts in two perpendicular planes that intersect along the main axis of the hemisphere.

In the first and second inserted positions of the first and second needles, the device is in an "inserted configuration" or "configuration of full insertion". In the first and second extracted positions of the first and second needles, the device is in an "extracted configuration".

"First" and "second", or "upper" and "lower", or "right-hand" and "left-hand" are used to distinguish corresponding elements, but do not limit the invention.

In the present description, unless otherwise stated, "comprise" does not involve an exclusivity.

BRIEF DESCRIPTION OF THE FIGURES

Other features and advantages of the invention will become clear upon reading the non-limitative following detailed description and by examining the non-limitative attached drawings, in which:

FIG. 12 schematically shows an exemplary device according to the invention with a drive mechanism;

FIG. 13 schematically shows an exemplary device according to the invention with a drive mechanism;

FIG. 14 schematically shows an exemplary device according to the invention with a synchronisation mechanism;

In the figures, identical reference signs are used to designate identical or similar elements.

DETAILED DESCRIPTION

Figure 1:
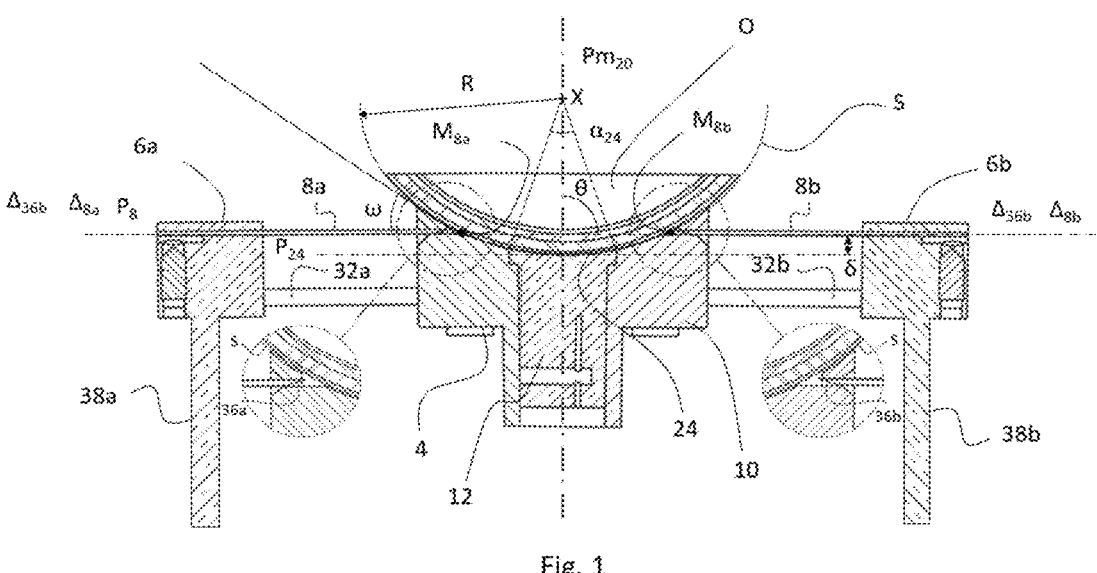
FIG. 1 schematically shows a device according to the invention.

A device according to the invention is particularly well adapted for electroporation. In this application, it preferably comprises an electric generator 2 configured for electroporation of a pharmaceutical composition, a support 4, and first and second combs 6a and 6b, which are mobile along a sliding direction $\Delta_6$.

The first and second combs 6a and 6b comprise first and second electrode needles 8a and 8b, respectively. All the electrode needles are electrically connected to a first terminal 9a of the electric generator 2. Together, they define an invasive electrode.

The support 4 comprises a support base 10 and a plate electrode 12 fixed on the support base and electrically connected to a second terminal 9b of the electric generator, which has a polarity opposite to the polarity of the first terminal.

The electrical generator is therefore adapted to polarize differently the plate electrode and the invasive electrode so as to generate an electrical field enabling electroporation.

Support

Support Base

The support base 10 is preferably in a polymeric material. It is preferably in a material which is not electrically conductive. It is preferably made of a transparent material for a better observation by the user.

The support base defines a spherical base contact surface 18 which extends along a virtual sphere S having a radius of curvature R between 10 mm and 15 mm, preferably between 11 mm and 14 mm, preferably between 12 mm and 13 mm, and is preferably about 12.5 mm. The virtual sphere S corresponds to the outside surface of an eye O so that, in the service configuration, the base contact surface can bear on this outside surface.

The stability of the support on the eye is therefore greatly improved.

To further improve the stability of the support on the eye, the spherical base contact surface 18 preferably bears one, preferably several spikes which are protruding from said surface and designed so as to limit the sliding of the support on the eye. The support preferably comprises more than 2, more than 5, more than 10, more than 20 spikes. The height of said spikes is preferably more than 0.1 mm and/or less than 0.5 mm or less than 0.3 mm.

Preferably, the base contact surface 18 has a surface area of greater than 50 mm², preferably of greater than 100 mm², preferably of greater than 120 mm², preferably of greater than 140 mm², preferably of greater than 150 mm², preferably of greater than 160 mm², and/or of less than 200 mm², preferably of less than 180 mm². Preferably, the base contact surface 18 does not extend over more than one quadrant of a hemisphere.

Seen from the front, the contact surface 18 can have a substantially parallelepipedal contour, for example a rectangular contour, or a substantially trapezoidal contour.

Preferably, the support base 10 defines a circular rim 20 which partially defines the limit of the contact surface 18, and extends in a rim plane $P_{20}$.

The rim 20 has the shape of an arc of a circle $C_{20}$ having an axis X and a radius $R_{20}$ of greater than 5 mm, preferably of greater than 5.5 mm, preferably of greater than 5.8 mm, and of less than 8.0 mm, preferably of less than 7.0 mm, preferably of less than 7.5 mm, preferably of less than 6.0 mm. Such a rim has a shape substantially corresponding to the limbus of the eye. It may be placed in contact with this limbus, so as to encircle partially said limbus.

The stability of the support is greatly improved when the rim 20 is designed to bear on the limbus of the eye.

Figure 2:
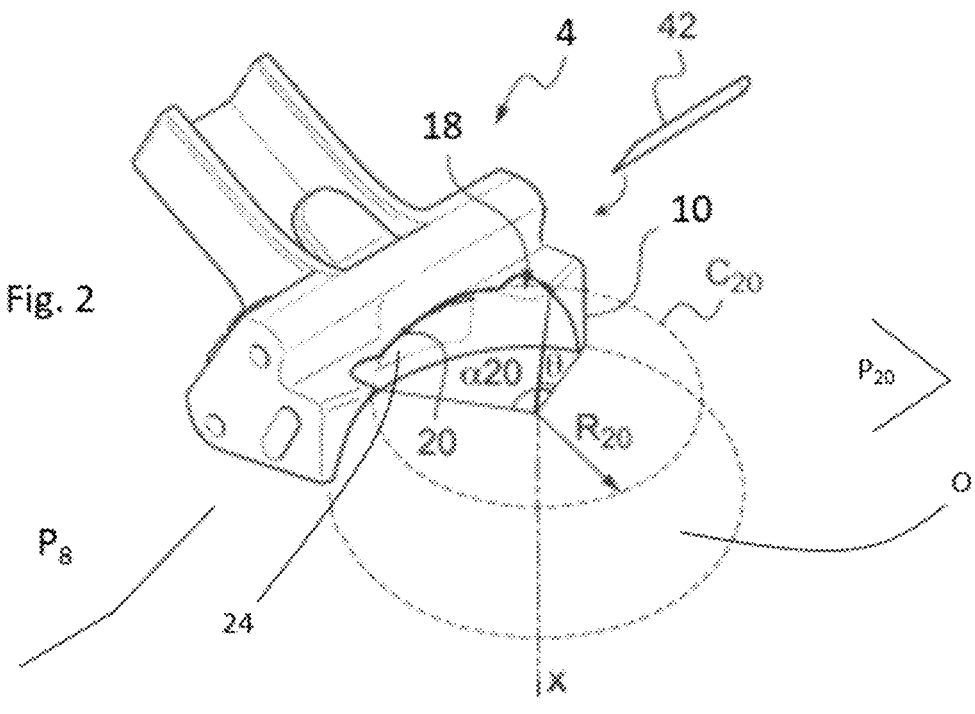
FIG. 2 shows in perspective an example of a device according to the invention contacting an eye.
Figure 3:
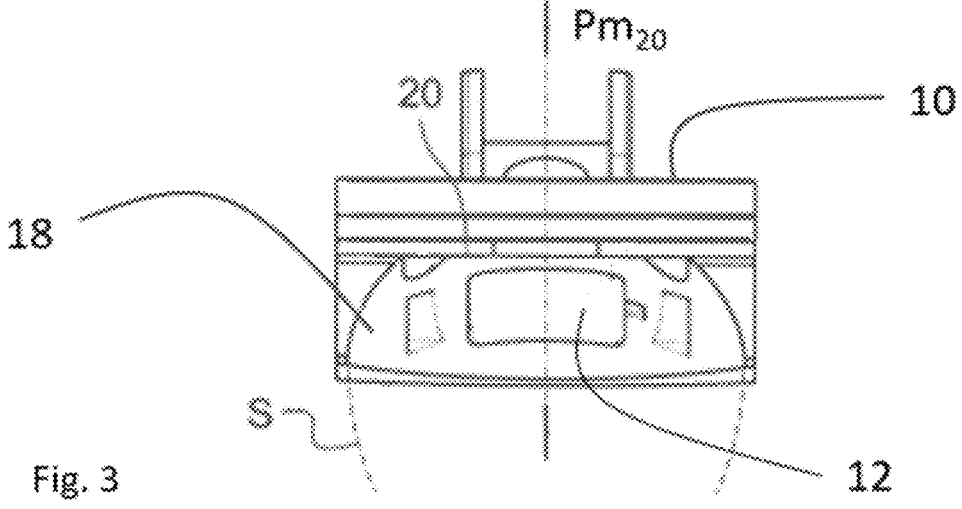
FIG. 3 shows an example of a device according to the invention, in a front view.
Figure 4:
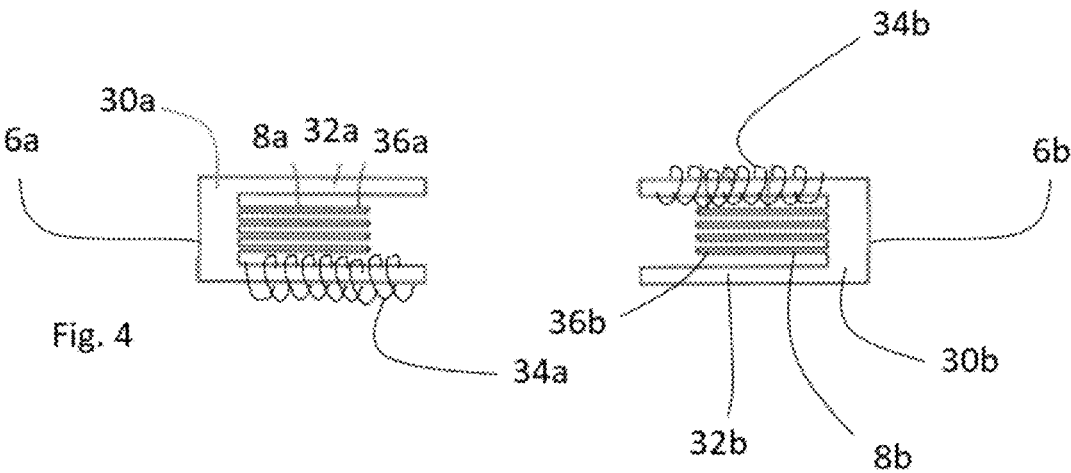
FIG. 4 represents the two combs of this device in the extracted position.

Preferably, the rim extends laterally over an angle sector $\alpha_{20}$ of greater than 45°, preferably greater than 60°, preferably greater than 80°, preferably greater than 100°, preferably greater than 120°, preferably greater than 130°, preferably greater than 135°, and/or less than 180°, preferably less than 170°, preferably less than 160°, preferably less than 150°, preferably less than 140° (see FIG. 2).

The support base preferably may comprise a support handle to be gripped, for example, between a thumb and an index finger of one hand. However, preferably, support handles are alternatively provided on the combs.

A Plate Electrode

The plate electrode 12 is fixed on the support base 10. It defines a plate electrode contact surface 24 which is intended to bear on the outside surface of the eye in the service position. It therefore preferably extends along the virtual sphere S, as represented, for instance, in FIG. 8.

The surface area of the plate electrode contact surface is preferably greater than 3 mm². greater than 4 mm². greater than 5 mm². greater than 6 mm². greater than 8 mm². greater than 10 mm² greater than 11 mm², greater than 12 mm². greater than 15 mm². greater than 17 mm², and/or less than 90 mm², less than 60 mm², less than 30 mm², less than 20 mm².

Preferably, the plate electrode contact surface 24 does not extend over more than one quadrant of a hemisphere. Preferably, it extends within an angular sector $\alpha_{24}$ around the axis X of the rim (see FIG. 1) which is less than 90°, preferably less than 60°, preferably less than 50°, preferably less than 45°, preferably less than 35°, preferably less than 30°, and/or preferably greater than 10°, preferably greater than 15°, preferably greater than 20°.

In a front view, the plate electrode contact surface has preferably a substantially rectangular shape.

The radius of curvature R is large relative to the surface area of the plate electrode contact surface, so that the plate electrode contact surface substantially extends in a general plate electrode plane $P_{24}$.

Preferably, the distance between the rim 20 and any point of the plate electrode contact surface 24 is greater than 2 mm, preferably greater than 2.5 mm, preferably greater than 3 mm, preferably greater than 3.5 mm, preferably greater than 4.0 mm, and/or less than 6 mm, preferably less than 5 mm, preferably less than 4.5 mm.

The plate electrode 12 may be an electrically conductive layer partly covering the support base. Preferably, it is not integral with the support base, i.e. is a part which is initially independent of the support base, then mounted onto the support base.

Combs

The first and second combs 6a and 6b are very similar, or identical, and assembled in the same way on the support, or in a very similar way, so that only the first comb and its arrangement are described in detail hereafter.

The references of the second comb are the same as the references of the first comb, but are indexed with ° b"instead of a".

The first comb 6a comprises a first comb base 30a, rectilinear first electrode needles 8a, fixed on the first comb base 30a;

preferably a first guiding rod 32a, fixed on the first comb base 30a, and preferably a first resilient member, for instance an helicoidal spring 34a or a blade spring, configured to force the first electrode needles toward their extracted position.

Preferably, all the first electrode needles have the same structure.

Preferably, the diameter of a first electrode needle, preferably of any first electrode needle is less than 0.5 mm, preferably less than 0.4 mm, preferably less than 0.35 mm. This characteristic is particulariy advantageous when the electrode needle is inserted into the eye substantially tangentially to the surface of the eye, as in the preferred embodiment. For the same reason, the first tip $36a$ of a first electrode needle, preferably of any first electrode needle is preferably bevelled.

The first comb may comprise one or several, preferably three, four or five, preferably four, preferably parallel, preferably coplanar, and preferably rectilinear first electrode needles $8a$. The distance between the axis of two adjacent parallel first electrode needles Ba is preferably greater than 0.5 mm, preferably greater than 0.6 mm, preferably greater than 0.7 mm, preferably greater than 0.8 mm, and/or less than 5 mm, preferably less than 3 mm, preferably less than 1.5 mm, preferably less than 1.2 mm, preferably less than 1.0 mm, preferably less than 0.9 mm.

Preferably, the first electrode needles Ba extend in a first needle plane $P_8$ which defines with the rim plane $P_{20}$ of the rim 20 an angle which is greater than 40°, greater than 45°, preferably greater than 50°, and/or less than 80°, preferably less than 70°, preferably less than 60°, preferably less than 55°.

The first needle plane $P_8$ is preferably substantially perpendicular to a median radial plane $Pm_{20}$ of the rim (angle $\theta$ of 90° in FIG. 1), i.e. a plane including the axis X and including the point at mid-length of the rim. Put differently, the first electrode needles are coplanar and preferably each extends substantially parallel to the plane $P_{20}$ of the rim.

The first electrode needles preferably each extend substantially parallel to the plate electrode 12. The angle between the first needle plane $P_8$ and the plate electrode plane $P_{24}$ is preferably less than 20°, preferably less than 15°, preferably less than 10° or less than 5°. The first needle plane $P_8$ is preferably substantially parallel to the plate electrode plane $P_{24}$.

The distance 6 between these two planes is preferably between 2.0 and 1.3 mm, preferably between 1.8 and 1.5 mm, preferably between 1.7 and 1.0 mm, preferably about 1.65 mm.

Each first electrode needle Ba is mobile and guided, by the sliding of a first guiding rod $32a$ in a guide of the support base 10, between an extreme (i.e. limited by an abutment) first inserted position and a first extracted position in which it is protruding and not protruding, respectively, inside the virtual sphere S.

Preferably, in the first inserted position, any first electrode needle defines, with the outside surface of the eye, an angle $\omega$ that is less than 40°, preferably less than 25°, preferably less than 10°. The first electrode needles therefore substantially penetrate tangentially into the eye.

Preferably, the length of the first electrode needles is determined so that, in the inserted position, in a front view, i.e. when observed perpendicularly to the first needle plane $P_8$, the first electrode needles Ba appear to substantially completely cross the plate electrode contact surface (i.e. substantially extend from one side to the opposite side of the plate electrode contact surface).

Preferably, the length of a first electrode needle is greater than 4 mm, preferably greater than 6 mm, preferably greater than 8 mm, preferably greater than 10 mm, preferably greater than 11 mm, and/or less than 15 mm, preferably less than 14 mm, preferably less than 13 mm.

Preferably, the first comb $6a$ comprises a first comb handle $38a$ extending substantially parallelly to the median radial plane of the rim, and preferably substantially perpendicular to the first needle plane $P_8$, so that the operator may push on the first comb $6a$ toward the support without being disturbed by the nose of a patient.

Preferably, the force which is required to move the first comb against the spring $34a$ is greater than 1 Newton, preferably greater than 4 Newton, and/or less than 20 Newton, preferably less than 10 Newton. Advantageously, the spring $34a$ limits the risk of injury when the operator manipulates the device.

The second comb is similar, and preferably substantially identical to the first comb. Preferably, the second comb base is configured so that, in the inserted position of the first and second needles, it is substantially symmetric with the first comb base relative to median radial plane of the rim.

Figure 5A:
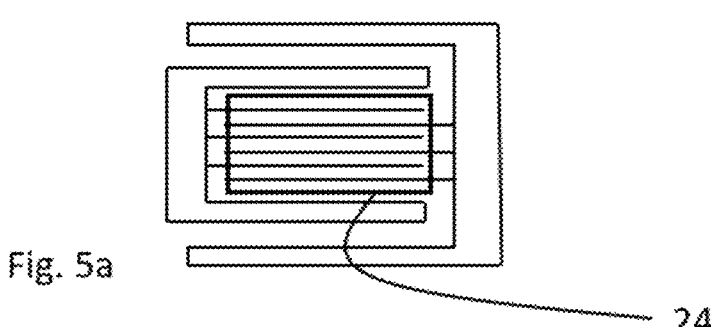
FIGS. 5a and 5b represent the two combs of the device in two examples of inserted positions.

The second electrode needles extend in a second needle plane which is parallel to the first needle plane, preferably identical to the first needle plane. To avoid collision between first and second electrode needles, their respective axis must then be offset. Preferably, they are interlaced with each other, i.e. in the needle plane, first electrode needles alternate with second needles, as represented in FIG. 5a.

Preferably, as represented in FIG. 1, the second comb $6b$ comprises a second comb handle $38b$, preferably parallel to the first comb handle $38a$. The convergence of the two combs toward the support, i.e. the movement in which the combs are pushed toward the support, is made easier and is possible with a single hand.

According to the invention, the two combs are slidable relative to the support so that, in a piercing position in which the plate electrode contact surface 24 bear on the outside surface of the eye, the rim 20 bears on the limbus of the eye, and the tips of the first and second electrode needles are bearing on the outside surface of the eye, said first and second tips can compress the eye when the first and second combs are simultaneously pushed toward the support 4.

In the piercing position, the first and second electrode needles extend along first and second insertion axis $\Delta_{8a}$ and $\Delta_{8b}$ and bear on the virtual sphere S on first and second insertion points $M_{8a}$ and $M_{8b}$.

All the first tips $36a$ of the first electrode needles exert, together, a first compression force $F_{36a}$, acting on a first compression point $M_{36a}$, along a first compression axis $\Delta_{36a}$.

All the second tips $36b$ of the second electrode needles exert, together, a second compression force $F_{36b}$, acting on a second compression point $M_{36b}$, along a second compression axis $\Delta_{36b}$.

The first and second compression axis $\Delta_{36a}$ and $A_{36b}$ are substantially parallel to the first and second insertion axis.

The angle between planes perpendicular to the first and second compression axis is preferably less than 40°, preferably less than 20°, preferably less than 10°, preferably less than 5°. The first and second compression axis are preferably parallel. Preferably, the distance between the first and second compression axis is less than 5 mm, preferably less than 3 mm, preferably less than 1 mm. Preferably, the first and second compression axis are aligned.

The risk of a rotation of the eye during the insertion of the electrode needles is thereby highly reduced.

Injection Needle

Preferably, the device comprises an injection needle 42. The injection needle may in particular have one or several characteristics of the injection needle disclosed in PCT/EP2016/058138, WO 2009/122030, or U.S. Ser. No. 12/921, 979, incorporated by reference. It preferably conventionally comprises an injection channel having an ejection orifice.

The injection needle is preferably not a first or a second electrode needle.

It is guided by the support base 10, between retrieved and injection positions. The injection position is preferably an abutment position defined so that the ejection orifice is between the first needle plane $P_8$ and the plate electrode plane $P_{24}$, preferably at mid-length between these planes, preferably so as to substantially face the centre of the plate electrode contact surface. In the injection position of the injection needle, the injection needle preferably extends parallel to the electrode needles.

Preferably, the injection needle is configured so that, when the plate electrode is extending in contact with the outside surface of the eye and the rim is extending on the limbus of the eye, and the injection needle is fully inserted, the ejection orifice of the injection needle opens in the ciliary muscle of the eye.

Pharmaceutical Composition

The injected product may be, in particular, any of the pharmaceutical compositions described in WO/2006/123248, incorporated by reference, and in particular a therapeutic nucleic acid of interest, preferably a desoxyribonucleic acid (DNA) molecule (cDNA, gDNA, synthetic DNA, artificial DNA, recombinant DNA, etc.) or a ribonucleic acid (RNA) molecule (mRNA, tRNA, RNAi, RNAsi, catalytic RNA, antisens RNA, viral RNA, etc.). In an embodiment, the composition contains a circular piece of DNA.

In a particularly preferred embodiment, the polynucleotide is a double-stranded, circular DNA, such as a plasmid, encoding a product with biological activity. Preferred biologically active agents include, but are not limited to, biologically active polypeptides or proteins disclosed in WO/2006/123248.

In another particular embodiment, the electroporation device of the invention is particularly suitable for performing gene replacement. Accordingly, the nucleic acid may encode for a viable protein so as to replace the defective protein which is naturally expressed in the targeted tissue. Typically, defective genes that may be replaced include, but are not limited to, genes that are responsible for the diseases disclosed in WO/2006/123248.

Kit

In accordance with the present invention, kits are envisioned. Such a kit comprises a device according to the invention and a pharmaceutical composition, and optionally instructions for use.

The pharmaceutical composition is preferably chosen among the pharmaceutical compositions which are described here above.

Within the kit, the components may be separately packaged or contained.

Instructions can be in written, video, or audio form, and can be contained on paper, an electronic medium, or even as a reference to another source, such as a website or reference manual.

Other components such as excipients, carriers, other drugs or adjuvants, instructions for administration of the active substance or composition, and administration or injection devices can be supplied in the kit as well.

Method

The method of the invention may be used for treating an ocular disease in a subject, the pharmaceutical composition being preferably chosen among the pharmaceutical compositions which are described here above.

To use the electroporation device according to the invention, an operator may proceed by the following steps:

First, the operator couples a reservoir filled with the pharmaceutical composition to the injection needle, and electrically connects the first electrode (all the electrode needles $8a$ and $8b$) and the second electrode (plate electrode 12) to the first and second terminals of the electrical generator 2.

Initially, the first and second electrode needles are in the first and second extracted positions and are preferably partly within the support base 10. The stiffness of the springs $34a$ and $34b$ is determined so that both first and second electrode needles are maintained in the extracted position, in particular, when the operator manipulates the device by the handles $38a$ and $38b$.

To position the device, the operator places the rim 20 on the limbus of the eye O. The placement of the rim 20 on the edge of the cornea and the bearing of the spherical plate electrode contact surface 24 on the sclera guarantee a good stability of the device and a very precise positioning. The stabilisation is very important in the present specific application, since the angles between the electrode needles $8a$ and $8b$, and/or injection needle 42 in one hand, and the spherical plate electrode contact surface in the other hand, are very low at the insertion points, i.e. the needles are inserted almost tangentially to this surface, which makes the insertion difficult.

The operator then pushes the first and second combs $6a$ and $6b$ toward each other, against the action of the first and second springs $34a$ and $34b$, respectively, until the piercing configuration, where the electrode needles are in their respective piercing positions, their respective tips contacting the outside surface of the eye.

In the piercing configuration, if the operator continues pushing the first and second combs $6a$ and $6b$ toward each other, he applies a compression on the eye. This compression results from the action of the first electrode needles, which is a first compression force acting on the first compression point $M_{36a}$, along a first compression axis $\Delta_{36a}$, with the counter action of the of the second electrode needles, which is a second compression force, acting on a second compression point $M_{36b}$, along a second compression axis $\Delta_{36b}$.

The spring stiffness is determined so that the tips of both the first and second electrode needles come into contact with the outside surface of the eye before any of them pierces it. Preferably, the force applied by the first spring $34a$ on the first comb $6a$ is the same as the force applied by the second spring $34b$ on the second comb $6b$, so that the tips of both the first and second electrode needles substantially simultaneously come into contact with the outside surface of the eye. In the piercing position, they, therefore, compress said surface, which efficiently prevents any rotation of the eye relative to the support base 10.

The operator then continues to push the first and second comb $6a$ and $6b$ toward each other, until the electrode needles pierce the outside surface of the eye.

The guiding rods $32a$ and $32b$ are slidably mounted on the support base 10 to guide the movement of electrode needles until they reach their respective inserted positions.

The first and second electrode needles then together define a grid which extends substantially parallel to the plate electrode contact surface 24, all along the length of the plate electrode contact surface 24.

Figures 23A, 23B, 23C, 23D:
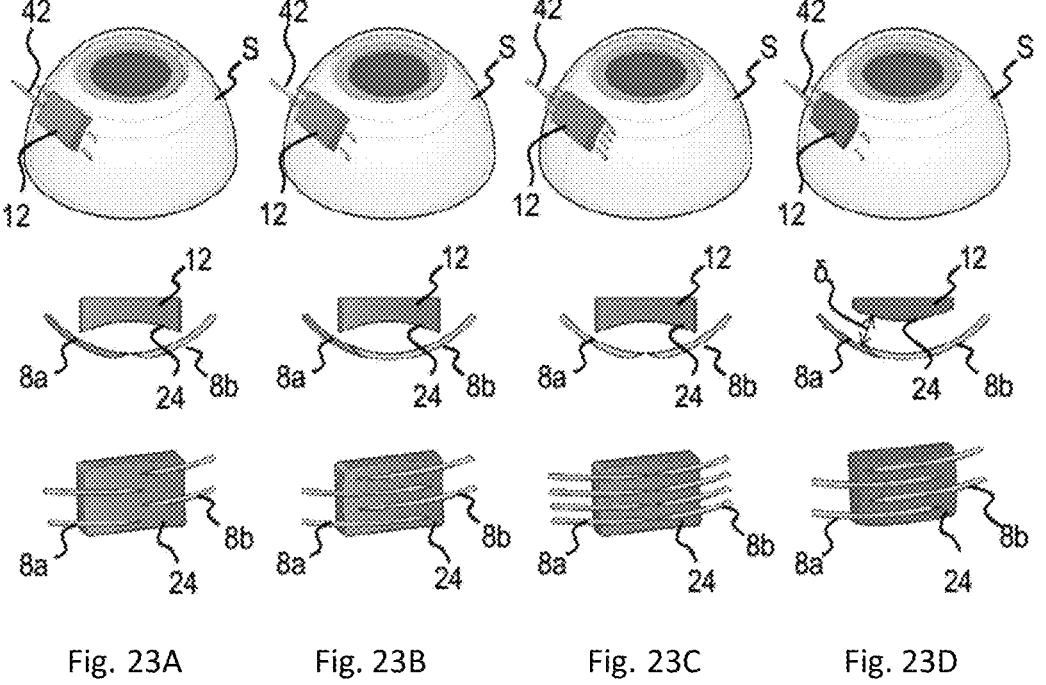
FIGS. 23A, 23B, 23C, and 23D schematically show different embodiments for the electrodes, in the service position (upper drawings), in a side view (middle drawings) and in perspective (lower drawings). The injection needle is only represented in the upper drawings.

Preferably, the first and second electrode needles are interlaced, as represented in FIG. 5a, 238, or 23D.

Figure 5B:
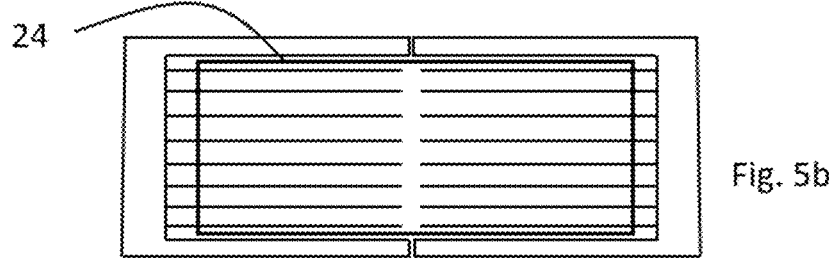
Figure 6:
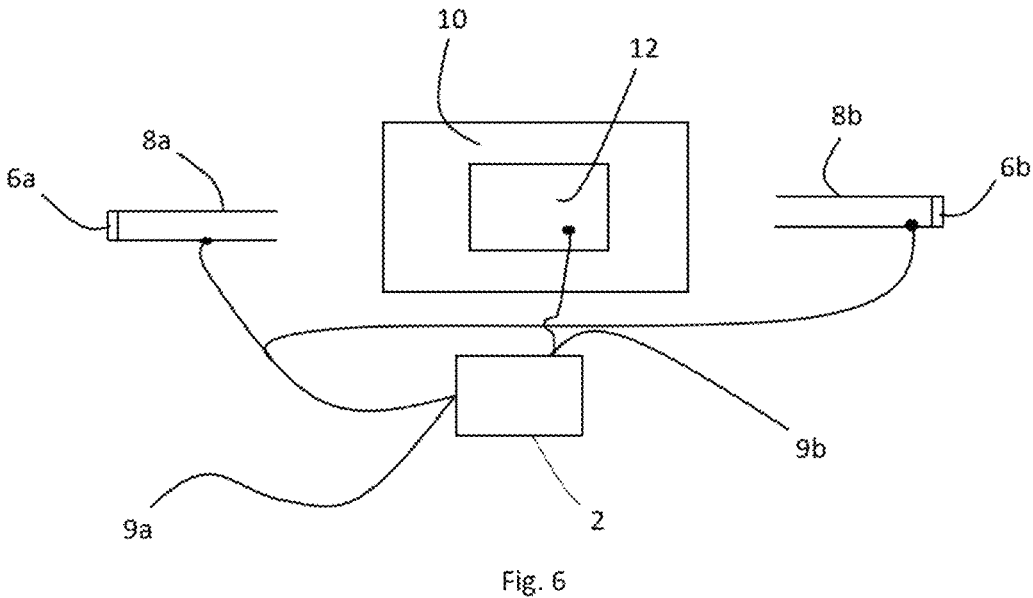
FIG. 6 represents the two electrodes according to the invention and a generator.
Figure 7:
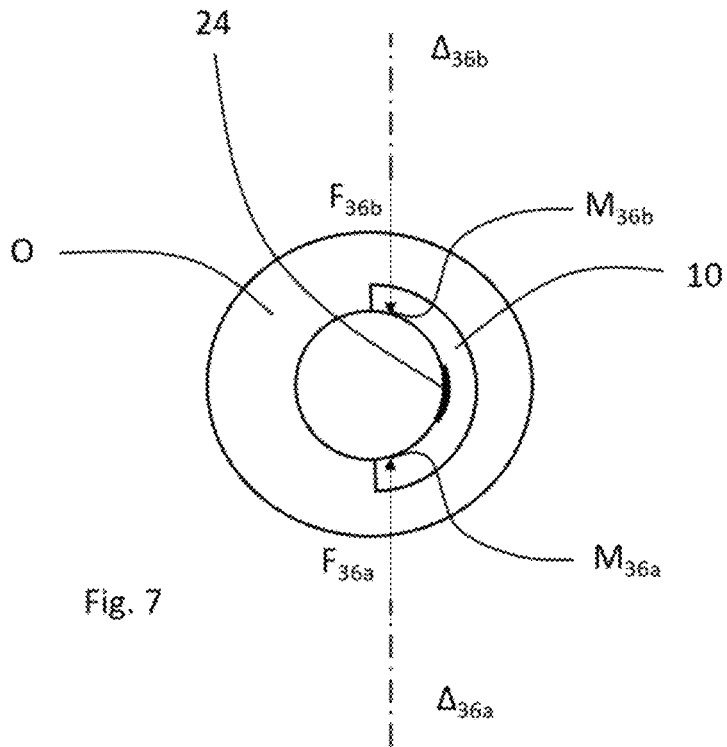
FIG. 7 schematically shows, in a front view, an eye having a device according to the invention in a piercing position.

Alternatively, in their respective inserted positions, the first and second electrode needles are not interlaced, but adjacent to each other as represented in FIG. 5b, 23A, or 23C. The distance between the tips of the first electrode needles, or "first tips", and the tips of the second electrode needles, or "second tips", is preferably less than 2 mm, 1 mm, less than 0.5 mm, preferably less than 0.2 mm. The first tips of the first electrode needles may be facing the second tips of the second electrode needles, as in FIGS. 5b and 23C, or not, as represented in FIG. 23C.

The operator then inserts the injection needle in the corresponding insertion guide, until a corresponding injection position. The previous insertion of the electrode needles enables a very stable position of the support during the insertion of the injection needle.

In an embodiment, the injection needle comprises a needle stop to determine an injection position in which the ejection orifice(s) open in the ciliary muscle, in front of the grid of the electrode needles, preferably in front of the centre of the grid.

The operator can then inject the composition.

The device is then in the service configuration and the operator sends a suitable electrical signal, for example suitable electrical impulses, by means of the electrical generator, in such a way as to create, within the injection zone, an electrical field that promotes electroporation.

In a particular embodiment, an electrical field constituted by one or more electrical pulse(s) is applied, as described in PCT/EP2016/058138.

When the electroporation of the product has been completed, the operator electrically disconnects the electrodes and the generator.

As is now clear, the device according to the invention permits a limitation or even a suppression of any rotation of the eye while the needles are being inserted therein;
the intervention of a single operator;
a precise and stable positioning of the electrodes;
a precise guidance of the invasive electrode during its penetration into the eye;
a precise injection into the eye relative to the limbus;
the generation of an efficient homogeneous large electrical field.

Of course, the invention is not limited to the embodiments described and shown, which have been provided by way of illustration.

In particular, the various embodiments could be combined.

Also, any feature of the device discloses in PCT/EP2016/058138 may be applied to a device according to the invention, unless is not compatible with the invention.

Also, the handling means are not limited to the comb handle 38a described hereabove.

In addition, the device preferably comprises a synchronization mechanism 50 to synchronize the movements of the first and second comb bases, from the first and second extracted positions to the first and second inserted positions respectively. Preferably, the synchronization mechanism 50 also synchronizes the movements of the first and second comb bases, from the first and second inserted positions to the first and second extracted positions respectively.

Preferably, the first and second comb bases are rotatably mounted on the support base around a common axis Y, and the device comprises a synchronisation linkage to mechanically link the movements of the first and second comb bases.

Figure 10:
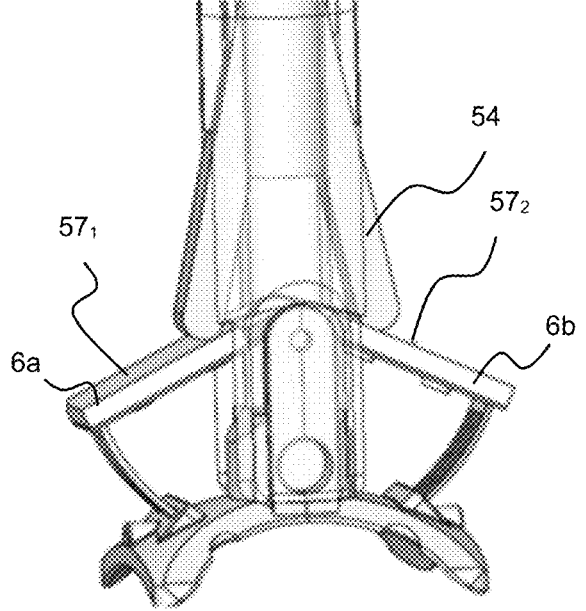
FIG. 10 schematically shows an exemplary device according to the invention with a synchronisation mechanism.
Figure 11:
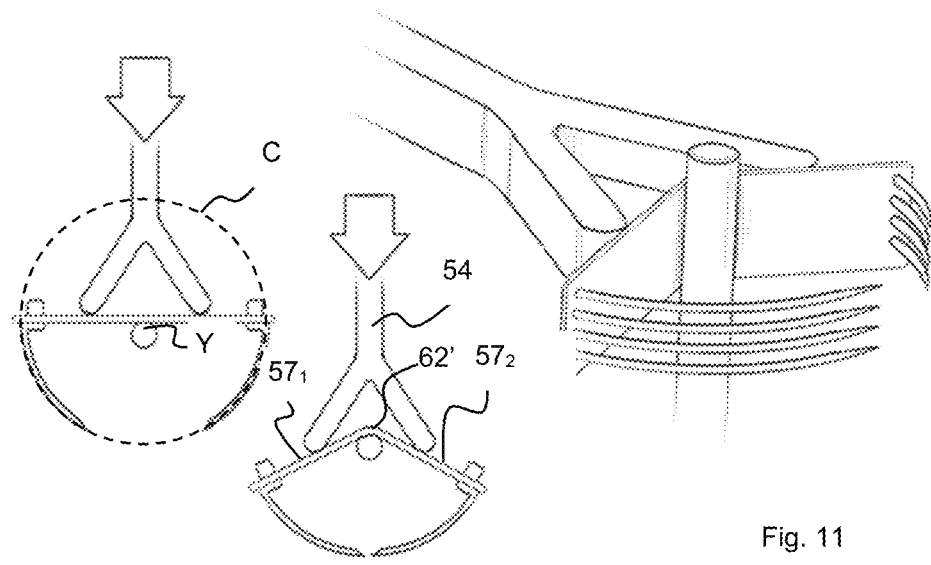
FIG. 11 schematically shows an exemplary device according to the invention with a synchronisation mechanism.

The synchronisation linkage preferably comprises a connector 54, preferably a rigid connector, configured to slide simultaneously on the first and second comb bases, preferably on first and second guide rails 56 of the first and second comb bases, respectively (FIGS. 8, 9), or on outside first and second surfaces 57$_1$ and 57$_2$ of the first and second comb bases (FIGS. 10, 11).

The connector 54 has preferably the shape of a "Y". In particular, first and second branches of the connector 54 may define the first and second pins 58 sliding in first and second guide rails 56 of the first and second comb (FIG. 8).

Figures 8, 9, 22:
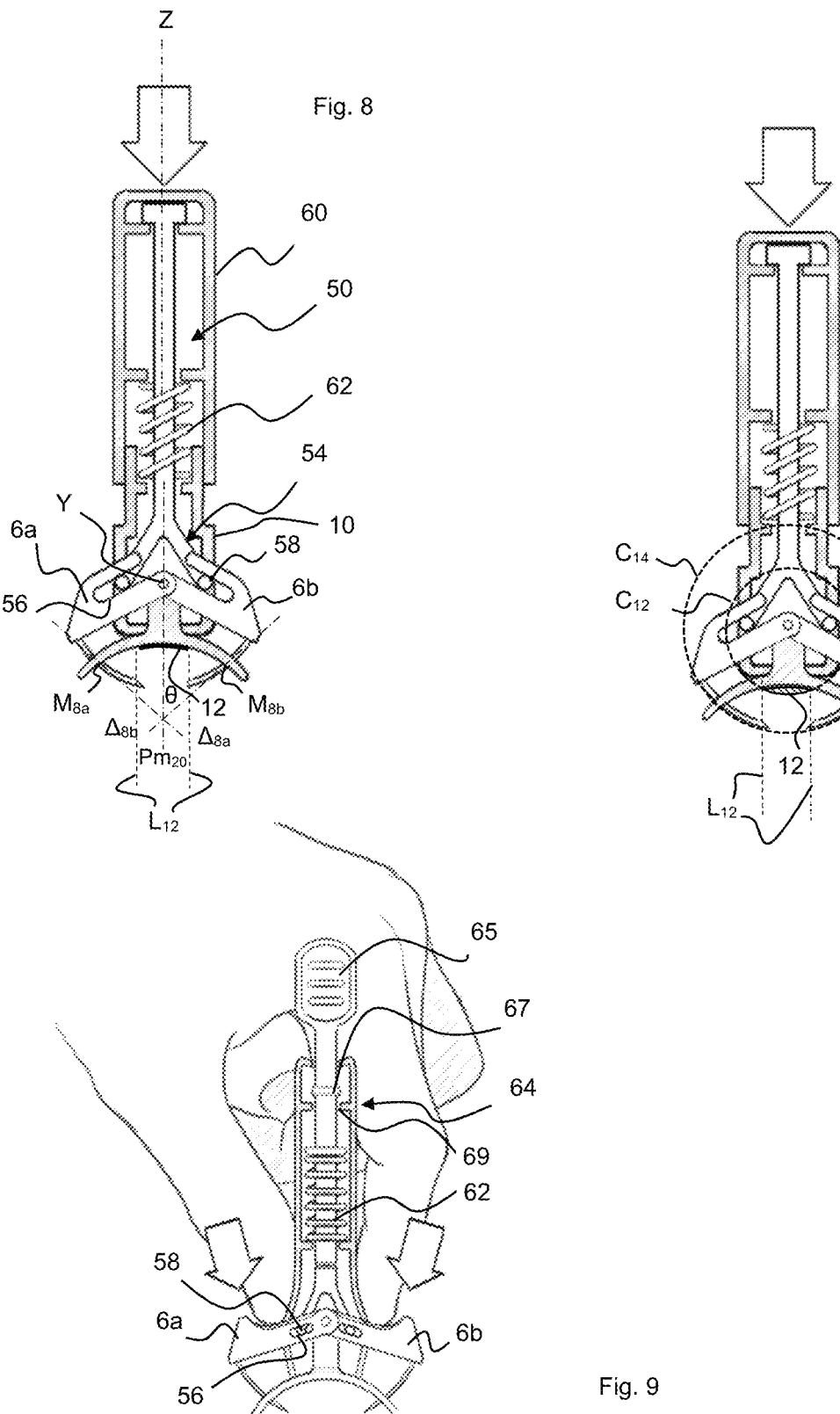
FIG. 8 schematically shows an exemplary device according to the invention with a synchronisation mechanism.
FIG. 9 schematically shows an exemplary device according to the invention with a synchronisation mechanism.
FIG. 22 schematically shows an exemplary device according to the invention with a convex plate electrode.

In particular, the device of FIG. 8 comprises a support base 10, a push button 60, slidably and elastically mounted on the support base 10, a connector 54 having the shape of a "Y", rigidly fixed to the button 60, and comprising first and second pins 58 cooperating with the first and second comb bases so that the sliding movement of the button 60 be coupled with movements of the first and second comb bases between the first and second inserted positions and the first and second extracted positions, respectively.

More precisely, the first and second comb bases are rotatably mounted on the support base around a common axis Y and define first and second guide rails 56 for the first and second pins 58 of the first and second branches of the connector 54, i.e. the branches forming an inversed "V". The translation of the rod 54 along its axis Z, relative to the support base 10 is thereby transformed into synchronized rotational movements of the first and second comb bases.

The device may comprise first and second arms 61$_1$ and 61$_2$ supporting the first and second comb bases, respectively, the movement of the second arm being guided relative to the first arm. Preferably the second arm is rotationally mounted on the first arm, around an axis W, in particular like two arms of a pair of scissors, as represented in FIG. 14.

Figure 15:
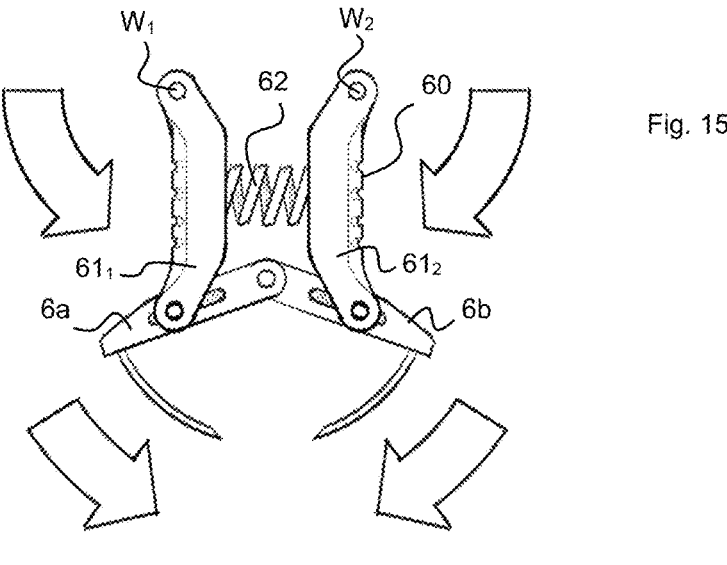
FIG. 15 schematically shows an exemplary device according to the invention with a synchronisation mechanism.

The movements of the first and second arms may be independent from each other. In particular, the first and second arms may be rotationally mounted on the support base around respective and different axis W$_1$ and W$_2$, as represented in FIG. 15.

Figure 16:
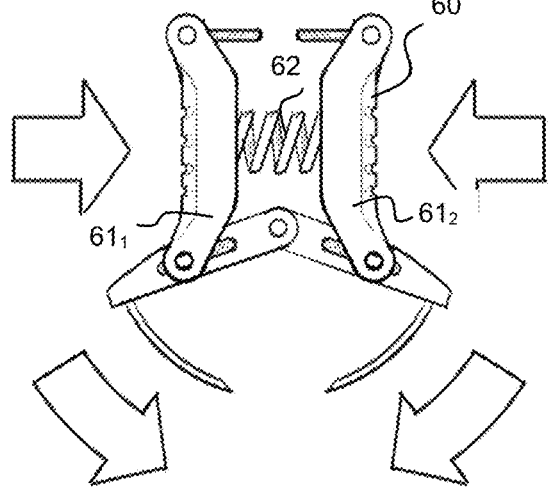
FIG. 16 schematically shows an exemplary device according to the invention with a synchronisation mechanism.
Figure 16:
Figure 17:
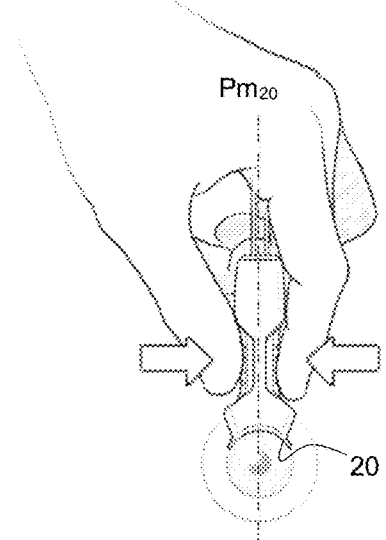
FIG. 17 schematically shows an exemplary device according to the invention with a synchronisation mechanism.

Alternatively, the first and second arms may be mounted on the support base to be mobile in translation relative to the support base, preferably along a common direction (horizontal direction in FIGS. 16 and 17), as represented in FIGS. 16 and 17.

Preferably, the first and second electrode needles are circularly shaped, i.e. extend along a circle C (see FIG. 11). The axis Y preferably intersects the centre of said circle. The insertion axis of a curved electrode needle is the local direction of the electrode needle at the insertion point. When the axis Y intersects the centre of said circle, the insertion axis of the first and second electrode needles therefore do not change during the insertion operation, so that the penetration of the first and second electrode needles is less harmful to the patient.

The operator may act directly on the comb bases, as in the example of FIG. 9 (see the arrows), and/or the device preferably comprises an actuator 60 to control the synchronization mechanism (FIG. 8 or 9, for example) or to directly act on the first and second comb bases (FIGS. 14 to 17). The actuator 60 may be, for instance, a push button, or a slider.

Preferably, the device comprises a spring 62 so as to automatically move the first and second electrode needles toward the first and second extracted positions, respectively. The action of the spring is therefore contrary to any action of the operator on the comb bases, directly or via the actuator, to insert the first and second electrode needles.

The spring 62 may be interposed between the synchronization mechanism and the support base, for example between the actuator 60 and the support base 10 (FIG. 8), or between the first and second comb bases.

In the embodiment of FIG. 11, the spring 62 is an elastic junction 62' linking the first and second comb bases. The first and second comb bases and the elastic junction may be a leaf spring.

In a preferred embodiment, the device comprises a deactivable lock 64 to lock the synchronization mechanism, preferably the actuator 60 or the connector 54, or, more generally the first and second electrode needles, in a configuration, preferably at least in the extracted configuration and/or in the inserted configuration.

In the embodiment of FIG. 9, the lock 64 is activated when the operator pulls on the tab 65, so that a bead 67 of the connector 54 is forced through an opening 69 of the base support.

In a preferred embodiment, the device comprises a drive mechanism 66 to control the insertion depth of the electrode needles during their insertion into the eye.

FIG. 12 illustrates an example of a drive mechanism 66 comprising a ratchet 68 configured to cooperate with a tooth 70 of a connector 54 so lock said connector in a predefined position. The number of predefined positions, i.e. the number of the ratchet teeth, is preferably greater than 2, 5 or 10 and/or less than 1000, 500, 100 or 50. The connector 58 may be unlocked by a pressure on a button 60, accessible to the operator through an opening 74 of the support base 10 (see the vertical arrow on FIG. 12). The opening 74 allows for a translation of the connector 58, relative to the support base 10, to change the position of the connector (see the horizontal arrow on FIG. 12).

FIG. 13 illustrates an example of a drive mechanism 66 comprising a rack 76, formed on the connector 54, and driven in translation by the teeth of a first pinion 78. In the embodiment of FIG. 13, a second pinion 80 is mechanically coupled with the first pinion 78 and with the actuator 60 (i.e. a thumb wheel) which is accessible to the operator through an opening 74 of the support base 10. When the operator turns the actuator 60, and therefore the second pinion 80 (see the arrow on FIG. 13), the connector 54 moves in translation.

Further Improvements

Summary of the Further Improvements

According to further improvements, the invention also relates to a device comprising:
a support comprising a support base defining
a spherical base contact surface extending along a virtual sphere having a radius between 10 and 15 mm to match an outside surface of an eye, and
a circular rim extending in a rim plane, having an axis X and a radius of greater than 5 mm and of less than 8 mm, so as to match the limbus of the eye;
a first needle having a first tip and being mobile on the support between
a first extracted position, in which the first needle is outside said virtual sphere, and
a first inserted position, in which the first needle is maximally inserted in the virtual sphere,
via a first intermediate piercing position in which the first tip is located on a first insertion point belonging to a first hemisphere of the virtual sphere,
the device comprising a counter base defining a counter contact surface extending along a second hemisphere of the virtual sphere, the first and second hemispheres being separated by the median radial plane of the rim,
the first needle being mobile on the support so that, during an insertion operation starting from the first extracted position and ending at the first inserted position, the first needle and the counter contact surface compress, or "pinch", the virtual sphere toward the median radial plane of the rim when the first needle reaches the first intermediate piercing position.

A device according to the further improvements may also have one or several of the following optional and preferred features:
the counter contact surface comprises a point which is symmetric, relative to the median radial plane of the rim, to the insertion point of the first needle;
the counter contact surface comprises a point which is at an intersection between the virtual sphere and a first insertion axis along which the first needle locally extends, at the first insertion point, in the first intermediate piercing position;
the counter contact surface bears at least one spike which is protruding from said counter contact surface and is configured so as to limit the sliding of the support on the eye, said spike having a height which is preferably greater than 0.1 mm and less than 0.5 mm;
the counter base is mobile on the support base, preferably rotatably mounted on the support base, or is fixed relative to the support base, the counter base being possibly a part of the support base;
the device comprises several first needles, preferably at least three first needles, preferably fixed on a common first comb base, extending parallelly to each other, preferably in a common first needle plane, so as to extend, in the first inserted position, substantially parallelly to a plate electrode contact surface defined by a plate electrode fixed on the support base and which extends along the virtual sphere;
the device comprises a synchronisation mechanism to synchronize, during the insertion operation, the movements of the first needle(s) and of the counter base.

This device may also comprise one or several features of the other embodiments of the invention.

Detailed Description of the Further Improvements

The basis of the invention is the "compression" of the eye, during the insertion operation of the electrode needles, to immobilize and stabilize the support on the eye. As described hereabove, according to the preferred embodiments of the invention, first and second combs are used for the compression.

In an alternative embodiment, all the electrode needles of the device are born by the first comb base, and the second comb is replaced by a counter base, to counter the action of the first electrode needles on the eye, i.e. to oppose a reaction to this action.

Figure 18:
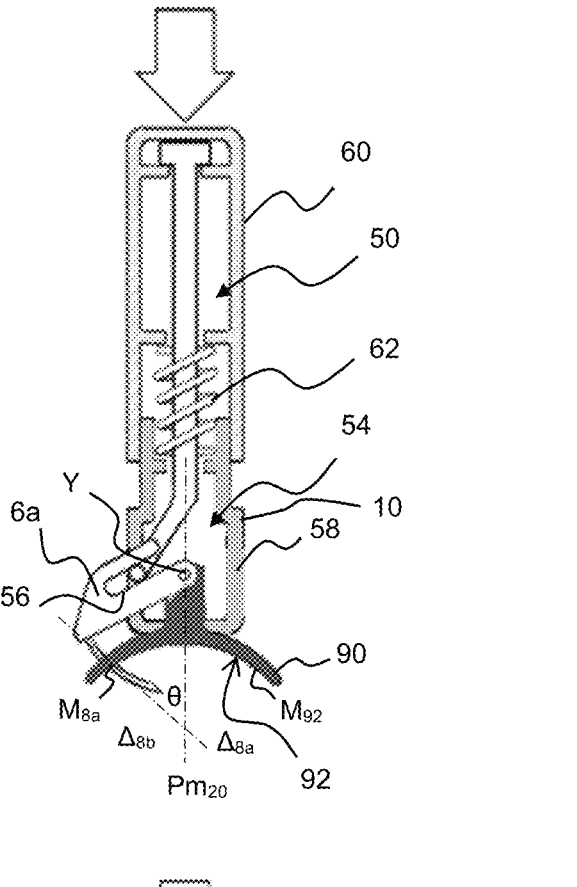
FIG. 18 schematically shows exemplary device according to the invention with a counter base.
Figure 19:
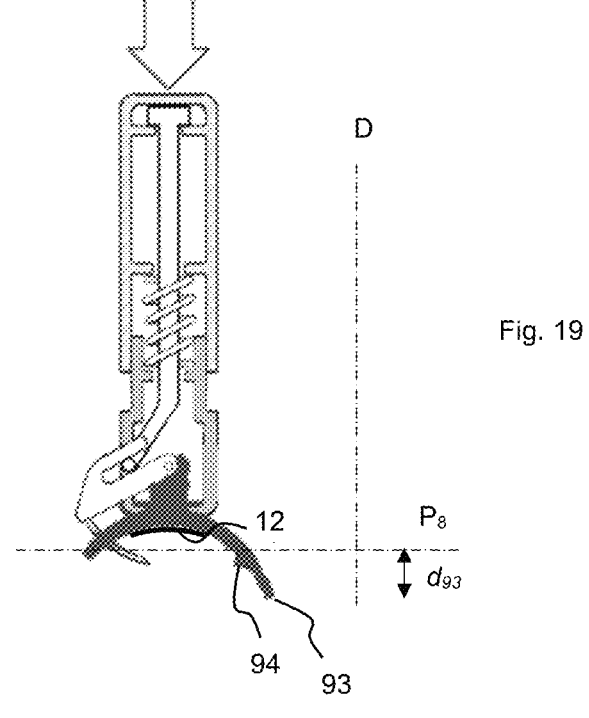
FIG. 19 schematically shows an exemplary device a cording to the Invention with a counter base.
Figure 20:
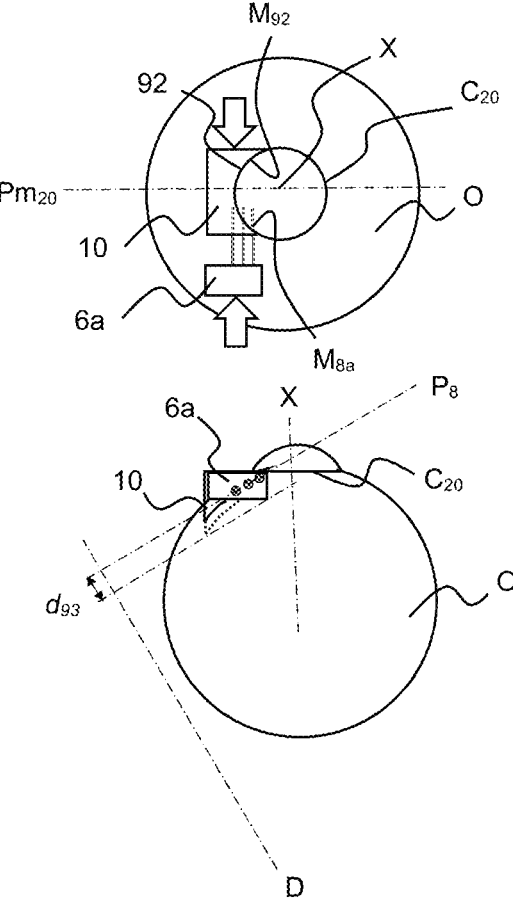
FIG. 20 schematically shows an exemplary device according to the invention with a counter base.

The counter base may be fixed relative to the support, at least during the insertion operation, as in the embodiment of FIGS. 18-20.

An example of such an alternative embodiment is illustrated in FIG. 18. This embodiment is similar to the embodiment of FIG. 8, but the second comb is replaced by a counter base 90. There are no second electrode needles.

All the previously described features which do not relate, directly or indirectly, to the second needles may be applied to this alternative embodiment.

The counter base 90 defines a counter contact surface 92 which comprises a point $M_{92}$ which is symmetric to the insertion point $M_{8a}$ of at least one first electrode needle, relative to the median radial plane of the rim $Pm_{20}$.

Preferably, the device comprises several parallel first electrode needles, fixed on a common first comb base. Preferably, first electrode needles are arranged so as to extend, in the first inserted position, in a plane facing the plate electrode 12, preferably substantially parallel to the plate electrode, as illustrated, for example, in FIG. 19.

Along to a direction D which is perpendicular to the general plane $P_8$ of the first electrode needles in the first inserted position (first needle plane), the counter contact surface 92 preferably extends beyond the insertion point $M_{8a}$, preferably extend beyond any insertion point of the first needles (see FIG. 19). Preferably, the distance $d_{93}$, along said direction D, between said insertion point and the extremity 93 of the counter contact surface 92 is greater than 1 mm, preferably greater than 2 mm, preferably greater than 3 mm, and/or less than 10 mm, preferably less than 5 mm.

The counter contact surface 92 is preferably part of the spherical base contact surface 18 of the support and extends along the virtual sphere S having a radius R between 10 and 15 mm to match the outside surface of an eye.

The counter contact surface 92 may have a smooth surface, without any roughness, preferably in a material that is not aggressive with respect to the surface of the eye, for example in a material made of polymers of silicone, of sponge, in particular synthetic sponge, of polyester, of polyorthoester, of polymethyl methacrylate or of any other flexible medical-grade polymers. Preferably, it bears one, preferably several spikes 94 which are protruding from said surface and are designed so as to limit the sliding of the support on the eye (FIG. 19). The counter contact surface 92 preferably comprises more than 2, more than 5, more than 10, more than 20, and/or less than 1000, 500, or 100 spikes 94. The height of said spikes is preferably more than 0.1 mm and/or less than 0.5 mm or less than 0.3 mm.

FIG. 20 illustrates an example embodiment of a device having a counter contact surface 92, in the service position on the eye O.

When the support base 10 is maintained on the eye of the operator and the operator pushes the first comb 6a toward the median radial plane of the rim $Pm_{20}$, i.e. when the first comb and the support base are pressed toward each other (see the large vertical arrows in FIG. 20), the counter contact surface 92 provides an at least partly antagonist force on the eye in reaction to the force exerted by the first needles.

Figure 21:
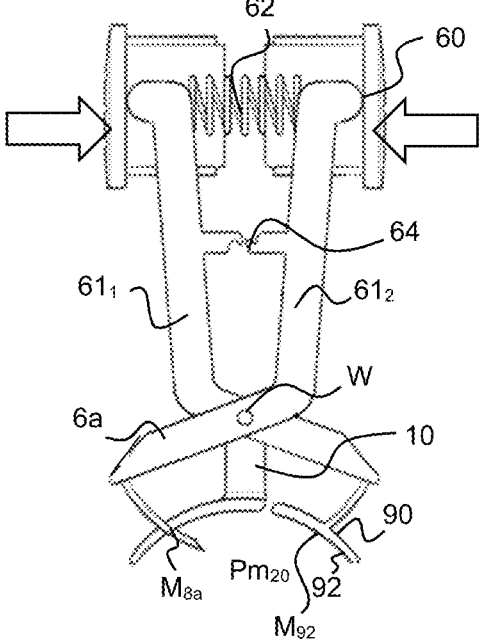
FIG. 21 schematically shows exemplary device according to the invention with a counter base.

The counter base may be mobile relative to the support base, at least during the insertion operation, as in the embodiment of FIG. 21.

This embodiment also illustrates how the movements of the first electrode needle(s) and of the counter base may be synchronized with a synchronisation mechanism similar to the mechanisms described previously to synchronize the movements of the first and second electrode needles during the insertion operation.

In an embodiment, the device comprises a said counter base, but also comprises second electrode needles, which may in particular be mobile on the counter base between the second extracted and inserted positions.

All the previously described features may also possibly be applied to this last embodiment.

Of course, the invention is not limited to the embodiments described and shown, which have been provided by way of illustration.

In particular, the various embodiments could be combined.

For any embodiment of the invention, the angle between:
a plane perpendicular to the axis X, and
a plane perpendicular to the general direction of the first needle(s) in the first inserted position,
is preferably greater than 70° and less than 110°, preferably greater than 80° and less than 100°.

For any embodiment of the invention, the angle between:
a plane containing the axis X and perpendicular to the median radial plane of the rim, and
the local direction of the first needle, preferably the local direction of any first needle, at the first insertion point of said first needle, in the first intermediate piercing position, and/or the general direction of the first needle(s) in the first inserted position,
is less than 45°, preferably less than 30°, preferably less than 20°, preferably less than 10°, preferably less than 5°, preferably about 0°.

When the plate electrode 12 extends along the spherical virtual sphere S (FIG. 8), it matches the surface of the eye, so that contact with the eye is uniform and comfortable, with a limited risk of injury.

But the plate electrode 12 does not necessarily extend along the spherical virtual sphere. In particular, it is advantageous that it extends parallel to the first and/or second needles when they are in the first and second inserted positions, respectively, i.e. so that the distance between the plate electrode and the portions of the first and/or second needles which are facing the plate electrode when they are in the first and second inserted positions, is constant. The region where the first and/or second needles are facing the plate electrode when they are in the first and second inserted positions are delimited by the vertical dotted straight lines $L_{12}$ in FIGS. 8 and 22.

Advantageously, the homogeneity of the electrical field between the invasive electrode made of the first and/or second needles and the plate electrode is improved.

In particular, in an embodiment, the first and/or second needles extend in a common plane when they are in the first and second inserted positions, and the plate electrode extends in a plane which is parallel to the plane of the first and/or second needles.

In an embodiment, the first and/or second needles extend along a common sphere $C_{14}$ when they are in the first and second inserted positions (see FIG. 22, or FIG. 23D), and the plate electrode 12 extends along a sphere $C_{12}$ which has the same centre as the a common sphere $C_{14}$. In this embodiment, the plate electrode 12 is therefore convex. It protrudes inside the virtual sphere S, for instance by a distance greater than 0.1 mm, 0.2 mm, or 0.5 mm. The distance 6 between the first and/or second needles and the plate electrode 12 is constant and is the difference between the radius of the sphere $C_{14}$ and $C_{12}$.

The invention claimed is:
1. A device comprising:
a support comprising a support base defining
   a spherical base contact surface extending along a spherical surface (S) having a radius (R) between 10 and 15 mm to match an outside surface of an eye, and
   a circular rim extending in a rim plane, having an axis X and a radius of greater than 5 mm and of less than 8 mm, so as to match the limbus of the eye;
a first needle and a second needle having a first tip and a second tip, respectively, the first tip and the second tip being oriented in opposing directions, and being mobile on the support between
   first and second extracted positions, in which the first and second needles are outside said spherical surface, respectively, and
   first and second inserted positions, in which the first and second needles are
   maximally inserted in the spherical surface, respectively,

via first and second intermediate piercing positions in which, respectively, the first and second needles extend along first and second insertion axes and the first and second tips are located on first and second insertion points belonging respectively to first and second hemispheres of the which are separated by a plane including the axis X and including a central point at mid-length of the rim, or median radial plane of the rim, the first and second needles being mobile on the support in opposing directions so that, during an insertion operation starting from the first and second extracted positions and ending at the first and second inserted positions, the first needle applies a first compression force and the second needle applies a second compression force which is a counter action to the first compression force, such that the first and second needles compress the spherical surface toward the median radial plane of the rim when they reach the first and second intermediate piercing positions, the first and second needles being curved.

2. The device according to claim 1, wherein the first and second needles extend along a common circle and are arranged so as to rotate on the support.

3. The device according to claim 2, wherein the first and second needles are arranged so as to rotate on the support around a common rotation axis, the distance between the centre of said circle and said rotation axis being less than 5 mm.

4. The device according to claim 1, comprising:

an electroporation generator comprising first and second terminals with different polarities, an invasive electrode electrically connected to the first terminal and comprising said first and second needles, a plate electrode fixed on the support, connected to the second terminal, and defining a plate electrode contact surface which extends along the spherical surface, wherein the first needle is curved and the plate electrode is curved so that the distance between any point of said first needle facing the plate electrode and the plate electrode is substantially constant, and/or the second needle is curved and the plate electrode is curved so that the distance between any point of said second needle facing the plate electrode and the plate electrode is substantially constant.

5. The device according to claim 1, comprising first and second arms supporting the first and second needles, respectively, the second arm being rotationally mounted on the first arm, around an axis, or the first and second arms being rotationally mounted on the support base around different respective axis, or the first and second arms being mounted to translate on the support base along a common direction.

6. The device according to claim 1, further comprising a spring elastically pushing the first and second needles toward the first and second extracted positions, respectively.

7. A device comprising:

a support comprising a support base defining a spherical base contact surface extending along a spherical surface(S) having a radius (R) between 10 and 15 mm to match an outside surface of an eye, and a circular rim extending in a rim plane, having an axis X and a radius of greater than 5 mm and of less than 8 mm, so as to match the limbus of the eye;

a first needle and a second needle having a first tip and a second tip, respectively, the first tip and the second tip being oriented in opposing directions, and being mobile on the support between first and second extracted positions, in which the first and second needles are outside said spherical surface, respectively, and first and second inserted positions, in which the first and second needles are maximally inserted in the spherical surface, respectively, via first and second intermediate piercing positions in which, respectively, the first and second needles extend along first and second insertion axes and the first and second tips are located on first and second insertion points belonging respectively to first and second hemispheres of the spherical surface which are separated by a plane including the axis X and including a central point at mid-length of the rim, or median radial plane of the rim, the first and second needles being mobile on the support in opposing directions so that, during an insertion operation starting from the first and second extracted positions and ending at the first and second inserted positions, the first needle applies a first compression force and the second needle applies a second compression force which is a counter action to the first compression force, such that the first and second needles compress the spherical surface toward the median radial plane of the rim when they reach the first and second intermediate piercing positions, further comprising a synchronisation mechanism to synchronize the movements of the first and second needles during said insertion operation.

8. The device according to claim 7, wherein the synchronisation mechanism comprises a connector having first and second branches mechanically coupled with first and second comb bases on which the first and second needles are rigidly fixed, respectively.

9. The device according to claim 8, wherein the first and second branches define first and second pins sliding in first and second guide rails defined by the first and second comb bases, respectively, or the first and second comb bases are linked by an elastic junction and the first and second branches are sliding on the first and second comb bases, respectively, so as to push said first and second comb bases against the action of the elastic junction.

10. The device according to claim 9, wherein the first and second comb bases and the elastic junction together constitute a leaf spring.

11. The device according to claim 7, further comprising a deactivable lock to lock the synchronization mechanism at least in an extracted configuration in which the first and second needles are in the first and second extracted positions and/or in an inserted configuration in which the first and second needles are in the first and second inserted positions.

12. The device according to claim 7, further comprising an actuator configured for an operator to act on the synchronisation mechanism, so as to simultaneously move the first and second needles.

13. The device according to claim 7, further comprising a drive mechanism defining a plurality of predetermined positions for the first and second needles.

* * * * *